US009186264B2

(12) United States Patent
Kramer et al.

(10) Patent No.: US 9,186,264 B2
(45) Date of Patent: *Nov. 17, 2015

(54) PROSTHETIC FOOT WITH MODULAR CONSTRUCTION

(71) Applicant: Tai Lore Made, LLC, Orlando, FL (US)

(72) Inventors: Leslie D. Kramer, Orlando, FL (US); William Stanley Patterson, Orlando, FL (US)

(73) Assignee: Tai Lore Made, LLC, Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/499,603

(22) Filed: Sep. 29, 2014

(65) Prior Publication Data

US 2015/0018976 A1  Jan. 15, 2015

Related U.S. Application Data

(63) Continuation of application No. 14/051,746, filed on Oct. 11, 2013, now Pat. No. 8,876,913.

(60) Provisional application No. 61/712,981, filed on Oct. 12, 2012.

(51) Int. Cl.
*A61F 2/50* (2006.01)
*A61F 2/66* (2006.01)
*A61F 2/76* (2006.01)

(52) U.S. Cl.
CPC .............. *A61F 2/6607* (2013.01); *A61F 2/66* (2013.01); *A61F 2/76* (2013.01); *A61F 2002/502* (2013.01);
(Continued)

(58) Field of Classification Search
CPC .............. A61F 2/50; A61F 2/60; A61F 2/66; A61F 2/6607; A61F 2/76; A61F 2/78; A61F 3/00; A61F 2002/5001; A61F 2002/5003; A61F 2002/5007; A61F 2002/5009; A61F 2002/502; A61F 2002/503; A61F 2002/5081; A61F 2002/5087; A61F 2002/509; A61F 2002/607; A61F 2002/608; A61F 2002/6614; A61F 2002/6621; A61F 2002/6628; A61F 2002/6635; A61F 2002/6642
USPC .................. 623/27, 38, 47–56, 28–30, 40–43
See application file for complete search history.

(56) References Cited

U.S. PATENT DOCUMENTS 2,475,372 A   7/1949   Catranis
3,551,914 A   1/1971   Woodall
(Continued)

FOREIGN PATENT DOCUMENTS

DE   327423   10/1920
DE   818828   10/1951
GB   114385   4/1918

OTHER PUBLICATIONS

International Search Report of Feb. 6, 2014 for PCT/US2013/064492.
(Continued)

*Primary Examiner* — Thomas J Sweet
*Assistant Examiner* — Christie Bahena
(74) *Attorney, Agent, or Firm* — Christopher M. Ramsey; GrayRobinson, P.A.

(57) ABSTRACT

A prosthetic foot includes a heel member having a heel member shaft extending upwardly from a heel end thereof and a forefoot member having a forefoot member shaft extending upwardly from a toe end thereof. An ankle member receives the heel member shaft and forefoot member shaft so as to allow the heel member shaft and forefoot member shaft to translate in a direction of a wearer's leg in response to an upward force thereon. At least one compressible member is coupled to the ankle member and is in compressible contact with the heel member shaft and/or forefoot member shaft so as to compress in response to the translation thereof.

18 Claims, 6 Drawing Sheets

(52) U.S. Cl.
CPC ... *A61F 2002/503* (2013.01); *A61F 2002/5003* (2013.01); *A61F 2002/5007* (2013.01); *A61F 2002/5083* (2013.01); *A61F 2002/5086* (2013.01); *A61F 2002/6614* (2013.01); *A61F 2002/6642* (2013.01); *A61F 2002/6664* (2013.01); *A61F 2002/6678* (2013.01)

(56) References Cited

U.S. PATENT DOCUMENTS

| | | | |
|---|---|---|---|
| 4,370,761 A | 2/1983 | Serri | |
| 4,547,913 A | 10/1985 | Phillips | |
| 5,376,133 A | 12/1994 | Gramnas | |
| 5,653,768 A | 8/1997 | Kania | |
| 5,766,264 A | 6/1998 | Lundt | |
| 6,129,766 A | 10/2000 | Johnson et al. | |
| 6,139,550 A | 10/2000 | Michelson | |
| 7,815,682 B1 | 10/2010 | Peterson et al. | |
| 7,862,622 B2 | 1/2011 | Dunlap et al. | |
| D655,009 S | 2/2012 | L'Heureux et al. | |
| 8,317,877 B2 | 11/2012 | Doddroe et al. | |
| 8,876,913 B2 | 11/2014 | Kramer et al. | |
| 2002/0143408 A1 | 10/2002 | Townsend et al. | |
| 2006/0069448 A1 | 3/2006 | Yasui | |
| 2012/0134742 A1 | 5/2012 | Changsrivong et al. | |
| 2012/0271434 A1 | 10/2012 | Friesen et al. | |
| 2013/0066439 A1 | 3/2013 | Zamora et al. | |
| 2013/0173023 A1 | 7/2013 | Lecomte et al. | |

OTHER PUBLICATIONS

Office Action of Aug. 1, 2014 for U.S. Appl. No. 14/051,746.
Office Action of Jul. 3, 2014 for U.S. Appl. No. 14/051,746.

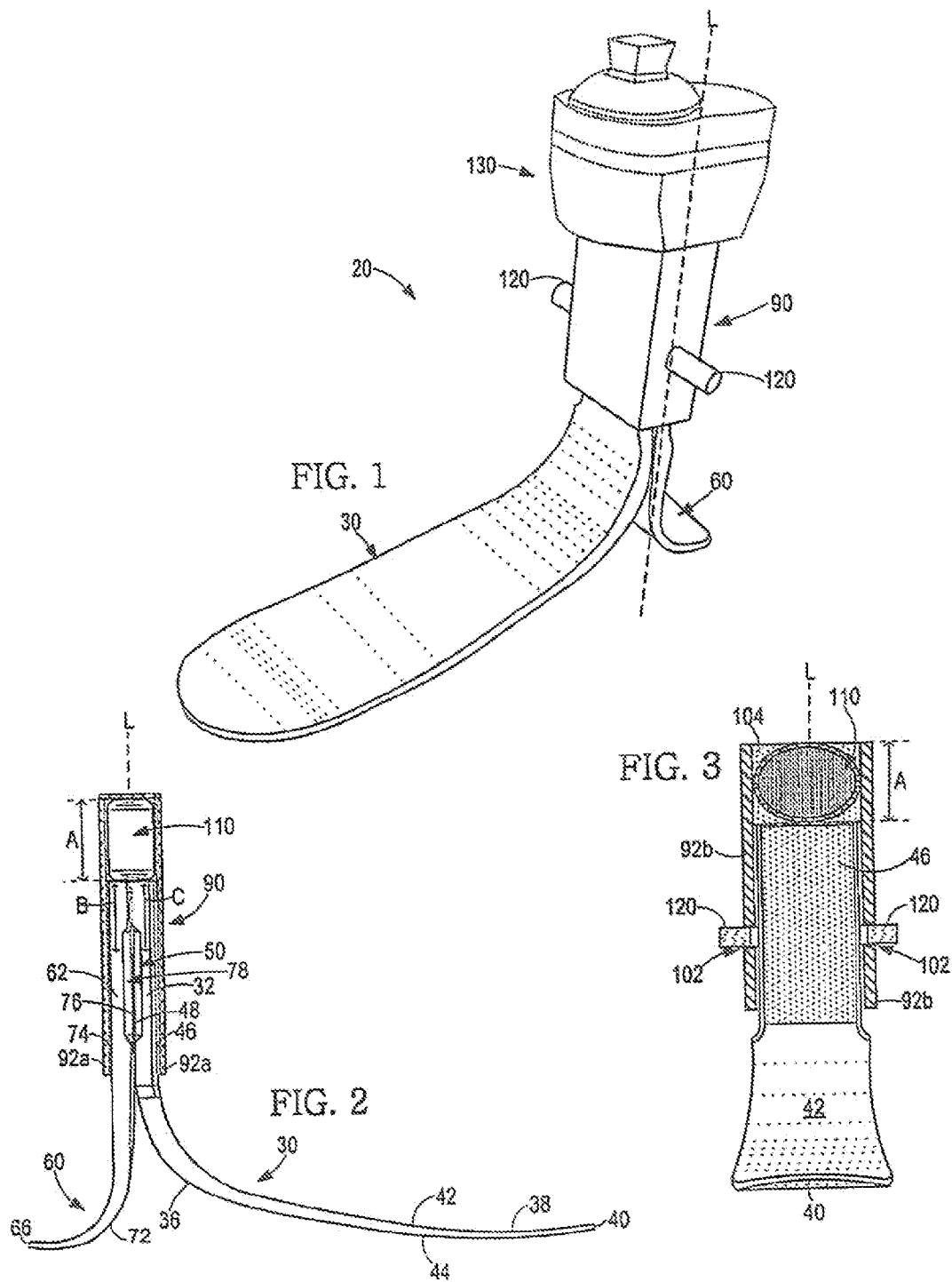

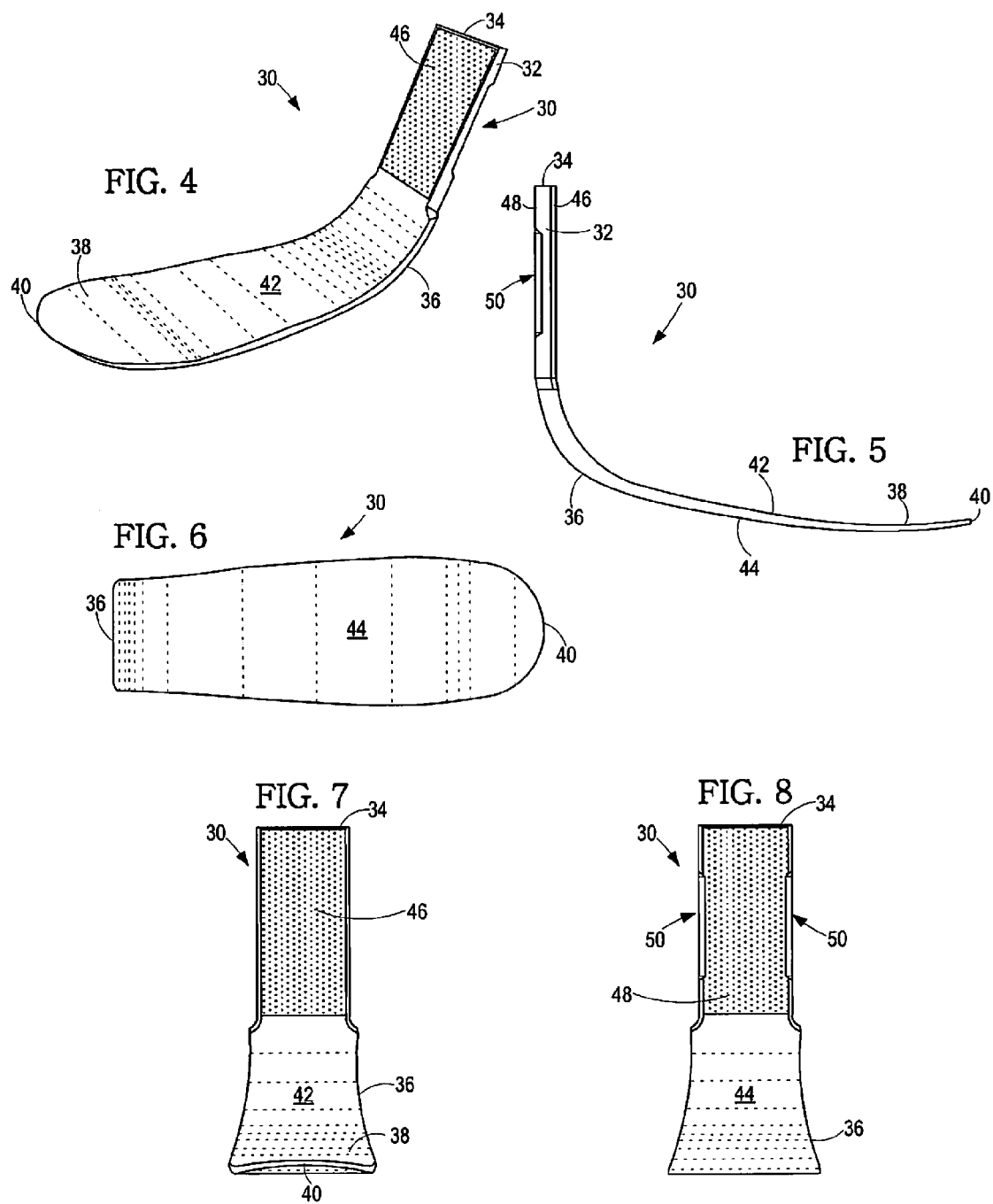

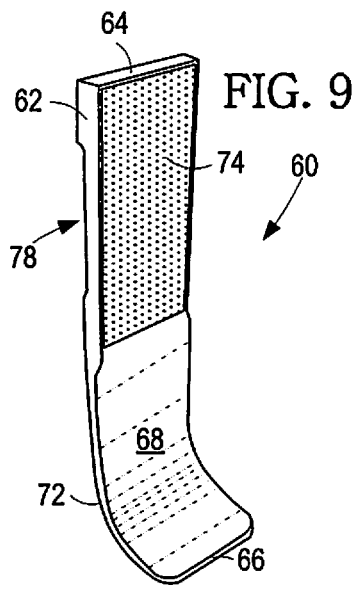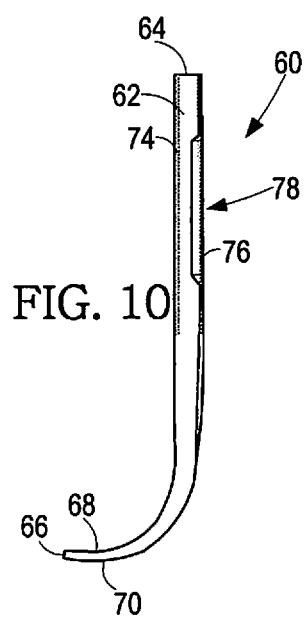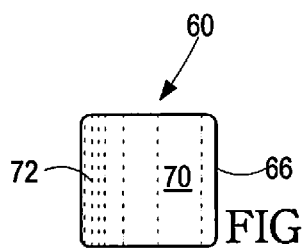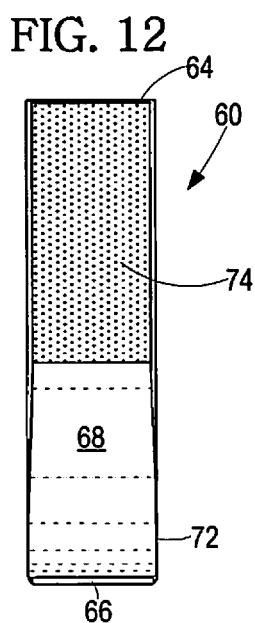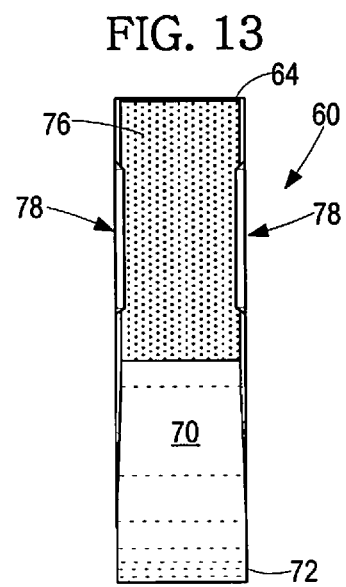

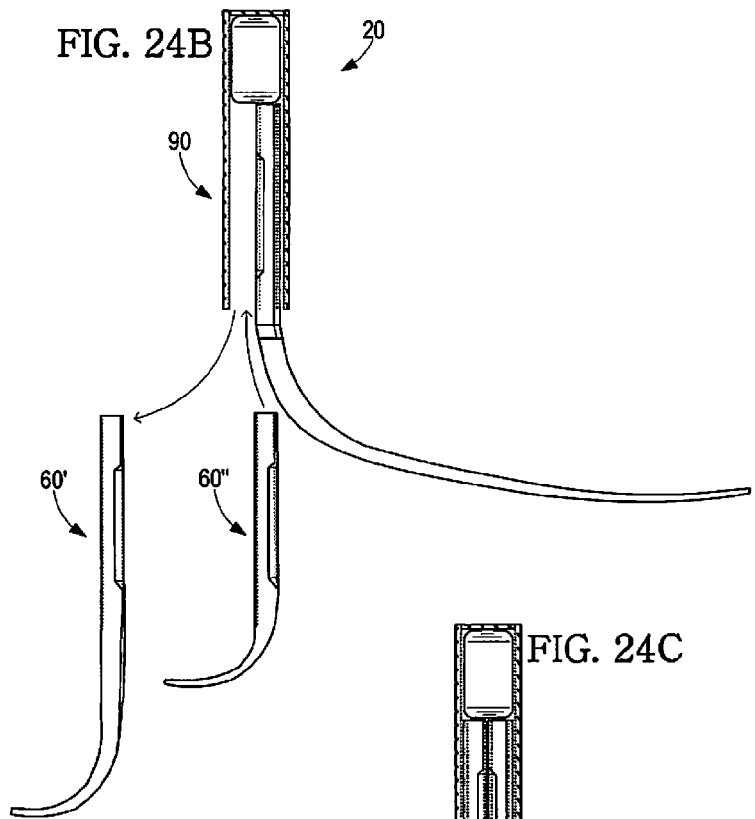
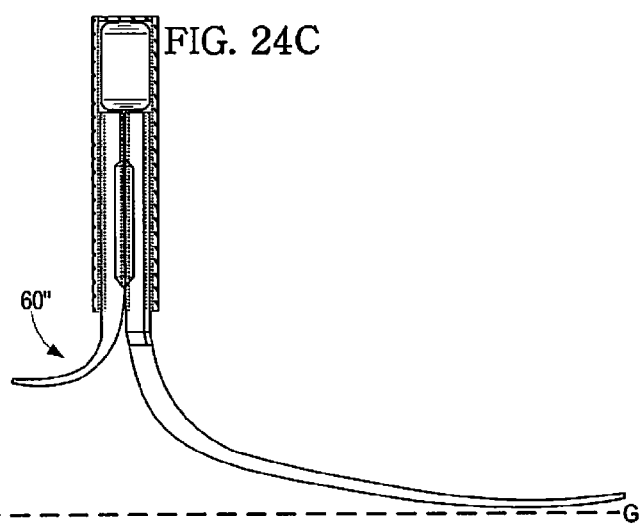
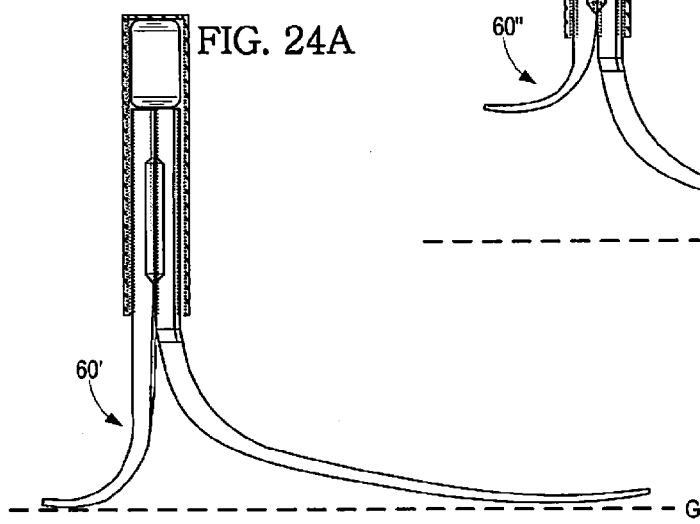

PROSTHETIC FOOT WITH MODULAR CONSTRUCTION

CROSS-REFERENCE TO RELATED APPLICATIONS

This is a continuation of application Ser. No. 14/051,746, filed Oct. 11, 2013, which claims priority to U.S. provisional application 61/712,981, filed Oct. 12, 2012 and titled "Prosthetic Foot with Interchangeable Components." The priority documents are incorporated by reference in their entireties.

FIELD OF THE INVENTION

The invention relates to prosthetic feet and, more particularly, to prosthetic feet made of interchangeable components.

BACKGROUND

Amputees that wear a prosthetic foot to enhance their mobility must choose a prosthetic foot that is appropriate for their size and lifestyle. Unfortunately, prosthetic feet that are designed for day-to-day activities such as walking are not ideal for performing vigorous exercise. For this reason, many amputees will have different prosthetic feet for different activities. In order to change between the different prosthetic feet when using conventional prosthetics, the amputee must completely remove the foot attached to the leg and replace it with a different foot. This is inefficient, expensive, and may change gait adjustments originally set by the attending prosthetist.

Conventional prosthetic feet are usually made of a plurality of components that are fastened together mechanically or with an adhesive to form a single structure. These are not designed to allow the wearer to replace different components, nor are they engineered to allow the amputee to replace, for example, walking foot components with running foot components without replacing the entire foot.

SUMMARY

In view of these problems, we have developed a prosthetic foot designed so that its components can easily be removed and replaced. The foot effectively allows wearers to have a single prosthetic foot that is adaptable to many different activities and sizes by selecting interchangeable components.

A first example of a prosthetic foot embodying these principles comprises a heel member having a heel member shaft extending upwardly from a heel end thereof and a forefoot member having a forefoot member shaft extending upwardly from a toe end thereof. An ankle member receives the heel member shaft and forefoot member shaft therein so as to allow the heel member shaft and forefoot member shaft to translate in a direction of a wearer's leg in response to an upward force thereon. At least one compressible member is coupled to the ankle member and in compressible contact with the heel member shaft and/or forefoot member shaft so as to compress in response to the translation of the heel member shaft and/or forefoot member shaft.

Other features of this first example may include the following.

The ankle member may apply inward force to the heel member shaft and forefoot member shaft to maintain an alignment of the heel member shaft and forefoot member shaft therealong.

The heel member shaft and forefoot member shaft may be translatable along the ankle member independently of one another.

The ankle member may form a sleeve around the heel member shaft and forefoot member shaft and the heel member shaft and forefoot member shaft may translate upwardly within the sleeve when upward force acts, respectively, on the heel member or forefoot member. In this case, the compressible member may be positioned above the heel member shaft and forefoot member shaft within the sleeve.

The ankle member may apply inward force to the compressible member when the compressible member is compressed to maintain the compressible member's alignment with the heel member shaft and forefoot member shaft.

The heel member shaft and forefoot member shaft may translate upwardly along the ankle member along or more guide slots defining the direction of translation, each guide slot having a corresponding pin inserted therein to restrict translation within a length of the one or more guide slots.

A second example of a prosthetic foot embodying these principles comprises an ankle member having a sleeve defining an interior extending along an axis defined by a wearer's leg and having a compressible member positioned therein; a heel member having a heel member shaft extending upwardly from a heel end thereof and along the axis within the interior; a forefoot member having a forefoot member shaft extending upwardly from a toe end and along the axis within the interior. The heel member shaft and forefoot member shaft are translatable along the axis in response to an upward force thereon. The compressible member compresses in response to the upward force.

Other features of the second example may include the following.

The ankle member may apply inward force to the heel member shaft and forefoot member shaft to maintain alignment of the heel member shaft and forefoot member shaft therealong.

The heel member shaft and forefoot member shaft may be translatable along the axis independently of one another.

The compressible member may be positioned above the heel member shaft and forefoot member shaft and intersect the axis.

The ankle member may apply inward force to the compressible member when the compressible member is compressed to maintain the compressible member's alignment with the heel member shaft and forefoot member shaft.

The extent of translatability may be defined by one more guide slots within the sleeve, extending along the axis, and having a corresponding pin inserted therein.

A third example of a prosthetic foot embodying these principles comprises an ankle member having a sleeve defining an interior extending along an axis defined by a wearer's leg, the interior being at least partially defined by anterior and posterior lubricated sidewalls; a heel member having a heel member shaft within the sleeve, a heel end extending downwardly out of the sleeve, and opposed lubricated anterior and posterior heel member surfaces, the lubricated posterior heel member surface being in slidable contact with the ankle member posterior lubricated sidewall; a forefoot member having a forefoot member shaft within the sleeve, a toe end extending downwardly and forwardly out of the sleeve, and opposed lubricated anterior and posterior forefoot member surfaces, the lubricated anterior forefoot member surface being in slidable contact with the ankle member anterior lubricated sidewall, the lubricated posterior forefoot member surface being in slidable contact with the lubricated anterior heel member surface; and a compressible member positioned within the interior above and in contact with the heel member shaft and forefoot member shaft so as to compress when upward force acts on the heel member and/or forefoot member.

Other features of the third example may include the following.

The heel member shaft and forefoot member shaft may together define a pair of opposed guide slots, each having a pin inserted therein to restrict the movement of the heel member and forefoot member to a length of the guide slots.

The pins may extend through opposed lateral sidewalls of the ankle member.

A pin securing member may apply inward force against the pins to maintain the pins within the guide slots.

The ankle member may apply inward force to the compressible member when the compressible member is compressed to maintain the compressible member's alignment with the heel member shaft and forefoot member shaft.

These and other objects, aspects, and advantages of the invention will be better appreciated in view of the following detailed description of preferred embodiments.

BRIEF DESCRIPTION OF THE DRAWINGS

FIG. 1 is a side anterior perspective view of a prosthetic foot connected to a limb connector, according to an embodiment of the invention;

FIG. 2 is a side view thereof with a lateral side of the ankle member cutaway;

FIG. 3 is a front view thereof with the anterior side of the ankle member cutaway;

FIG. 4 is a side anterior perspective view of an exemplary forefoot member useful with the prosthetic foot of FIG. 1;

FIG. 5 is a side elevation of the forefoot member of FIG. 4;

FIG. 6 is a bottom view of the forefoot member of FIG. 4;

FIG. 7 is an anterior elevation view of the forefoot member of FIG. 4;

FIG. 8 is a posterior elevation view of the forefoot member of FIG. 4;

FIG. 9 is a side posterior perspective view of an exemplary heel member useful with the prosthetic foot of FIG. 1;

FIG. 10 is a side elevation view of the heel member of FIG. 9;

FIG. 11 is a bottom view of the heel member of FIG. 9;

FIG. 12 is a posterior elevation view of the heel member of FIG. 9;

FIG. 13 is an anterior elevation view of the heel member of FIG. 9;

FIGS. 24A-C illustrate an example of how components of the prosthetic foot of FIG. 1 can be interchanged.

DETAILED DESCRIPTION OF PREFERRED EMBODIMENTS

Figure 14:
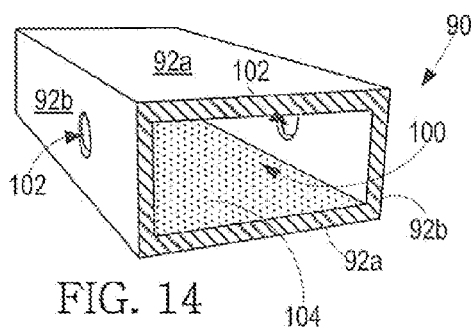
FIG. 14 is a bottom perspective view of an exemplary ankle member useful with the prosthetic foot of FIG. 1.
Figure 15:
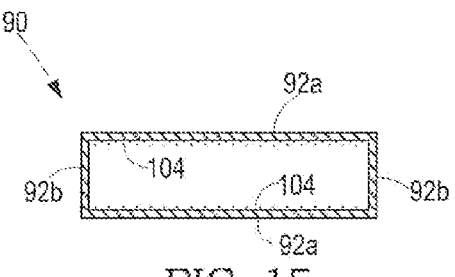
FIG. 15 is a bottom view of the ankle member of FIG. 14.
Figure 16:
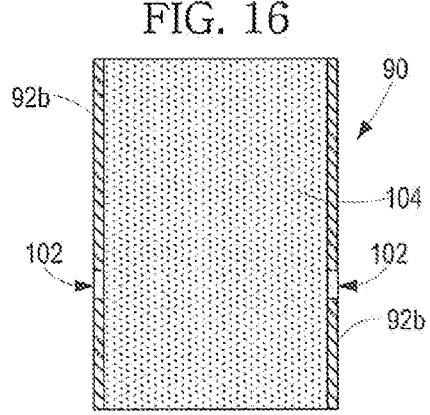
FIG. 16 is anterior or posterior side elevation view of the ankle member of FIG. 14 with the facing side cutaway.
Figure 17:
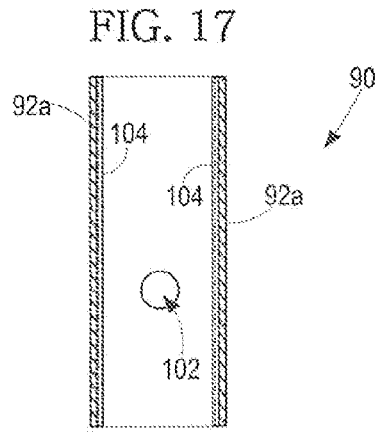
FIG. 17 is a lateral side elevation view of the ankle member of FIG. 14 with the facing side cutaway.

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein. Rather, these embodiments are provided so that this disclosure will convey preferred embodiments of the invention to those skilled in the art.

FIG. 1 generally illustrates a prosthetic foot 20 according to an embodiment of the invention. The foot 20 includes a forefoot member 30, a heel member 60, and an ankle member 90. In practice, the foot 20 is attached to a limb connector 130 designed to connect the foot to the wearer's leg. The wearer's leg defines a vertical axis L along which the ankle member 90 is aligned. The limb connector 130 is shown in broken lines to indicate that its design does not form a key component of the foot 20. The foot 20 may function regardless of the type of limb connector 130 used.

The prosthetic foot 20 is modular and includes parts that can be removed and substituted very easily to meet the individual needs of the wearer. This allows the components to be interchanged with other components for the purpose of replacement or for the purpose of substituting one component for another component having different properties. For example, the original forefoot and heel members may be interchanged with different forefoot and heel members suited to a particular activity, the wearer's gait, the wearer's lifestyle, a particular shoe size, the wearer's height, the wearer's weight.

In FIGS. 2 and 3 the facing side of the ankle member is cutaway so that the mechanical functionality of various components is revealed. The details of each component are discussed in turn.

The ankle member 90 forms a sleeve into which a forefoot member shaft 32 and heel member shaft 62 are positioned. The ankle member 90 applies inward force against the forefoot member shaft 32 and heel member shaft 62 to maintain alignment of the respective shafts 32, 62 along the vertical axis of the ankle member 90. The forefoot member shaft 32 and heel member shaft 62 slide independently along the ankle member when upward force acts on the forefoot member 30 or heel member 60.

A compressible member 110 is coupled to the ankle member 90 and is in compressible contact with the heel member shaft 62 and forefoot member shaft 32 so as to compress when upward force acts on the heel member 60 and/or forefoot member 30. The vertical arrow A in FIGS. 2 and 3 illustrates that the compressible member 110 compresses along the direction of the vertical axis of the ankle member 90. The vertical arrows B and C illustrate the direction the shafts 32, 62 slide along the ankle member 90.

When upward force acts on the heel member 60 or forefoot member 30, the respective shaft 32, 62 slides vertically within the ankle member 90 and compresses the compressible member 110, which absorbs the shock due to the force. The heel member shaft 62 and forefoot member shaft 32 slide independently of one another along the ankle member 90 because the only mechanical link between the shafts 32, 62 is the inward force applied by ankle member 90.

The heel member 60 can easily be removed from the ankle member 90 by sliding it out of the ankle member 90. Likewise, the forefoot member 32 can easily be removed from the ankle member 90 by sliding it out of the ankle member 90. Either of these components can then be replaced with a different heel member 60 and/or forefoot member 30 that suits a certain activity or weight without needing to remove the ankle member 90 from the wearer's limb. This also allows worn components to be replaced without needing to replace the entire foot or send the foot back to the manufacturer for repair.

Additional details of a preferred forefoot member 30 are shown in FIGS. 4-8. The forefoot member 30 includes the forefoot member shaft 32 and extends from a forefoot member upper end 34 through a curved forefoot section 36 to a toe section end 38 and terminates at a toe end 40. A forefoot member top surface 42 and forefoot member bottom surface 44 are positioned on opposite sides.

At the shaft section 32, the forefoot member top surface 42 includes a lubricated forefoot member anterior surface 46. Also at the shaft section 32, the forefoot member bottom surface 44 includes a lubricated forefoot member posterior surface 48.

The opposed lateral sides of the forefoot member each include an elongated depression 50 formed along the shaft 32 adjacent to the lubricated forefoot member posterior surface 48.

Additional details of a preferred heel member 60 are shown in FIGS. 9-13. The heel member 60 includes the heel member shaft 62 and extends from a heel member upper end 64 through a curved heel section 72 to a heel end 66. A heel member top surface 68 and heel member bottom surface 70 are positioned on opposite sides.

At the shaft section 62, the heel member top surface 68 includes a lubricated heel member posterior surface 74. Also at the shaft section 62, the heel member bottom surface 70 includes a lubricated heel member anterior surface 76.

The opposed lateral sides of the heel member 60 each include an elongated depression 78 formed along the shaft 62 adjacent to the lubricated heel member anterior surface 76.

Additional details of a preferred ankle member 90 are shown in FIGS. 14-17. The ankle member 90 forms a sleeve having opposed anterior and posterior sidewalls 92a and opposed lateral side walls 92b that together define an interior 100. The interior surface along the anterior and posterior sidewalls 92a is lubricated to form anterior and posterior lubricated sidewalls 104. In the embodiment shown, the ankle member 90 is symmetric about a vertical plane bisecting the anterior and posterior sidewalls 92a and a vertical plane bisecting the lateral side walls 92b.

Both lateral sidewalls 92b define a respective opening 102 that passes through to the interior 100. The purpose of the openings 102 is described in detail below.

Figure 18:
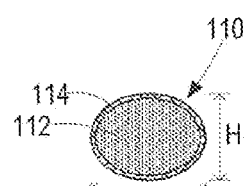
FIG. 18 is a top view of the of an exemplary compressible member useful with the prosthetic foot of FIG. 1.
Figure 20:
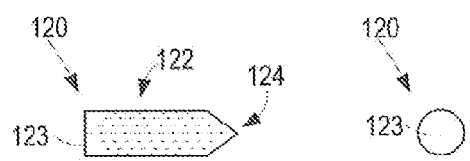
FIG. 20 is a side elevation view of an exemplary pin useful with the prosthetic foot of FIG. 1.
Figure 22:
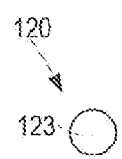
FIG. 22 is a rear elevation view of the pin of FIG. 20.
Figure 19:
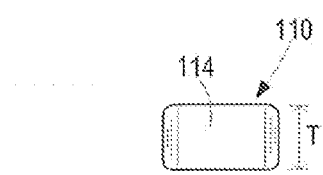
FIG. 19 is a side elevation view of the compressible member of FIG. 18.
Figure 21:
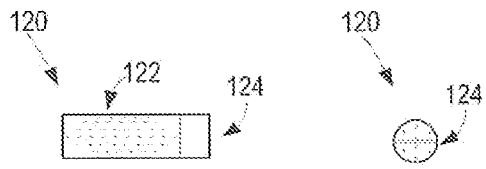
FIG. 21 is a top or bottom view of the pin of FIG. 20.
Figure 23:
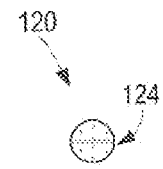
FIG. 23 is a front elevation view of the pin of FIG. 20.

Additional details of the preferred compressible member 110 are shown in FIGS. 18 and 19. The compressible member 110 is adapted to compress in the vertical direction and return to its original shape when the compression force is removed. Accordingly, the compressible member 110 functions in a spring-like manner to absorb the shock on the heel member 60 and forefoot member 30 when the wearer uses the prosthetic foot.

In the example shown, the compressible member 110 forms an elongated disk-like shape with a compressible material 112 in a high flexure and fatigue resistant material sheath 114. The compressible material 112 is preferably rubber, plastic, or the like. The sheath 114 is preferably also rubber, plastic, or the like. The make-up of the compressible material 112 is specifically selected for the degree of energy recovery required to match the wearer's lifestyle and body weight. The material property combinations for the compressible material 112 material and sheath 114 determine the energy recovery performance of the compressible member 110. These materials may be selected to provide a specific type of shock-absorbing performance tuned to a wearer's preference.

When the compressible member 110 compresses, it recovers energy from the heel member 60 and forefoot member 30 and returns a significant amount of that energy back to the heel member 60 and forefoot member 30 to allow the wearer to have a more natural stride. The compressible member 110 also returns rapid shock induced energy, from jumping for example, in a controlled manner. If the compressible member 110 becomes overloaded or fatigued and the sheath 114 fails, the compressible member 110 will not totally fail because the compressible material 112 will remain intact.

The shape of the compressible member 110 is selected to fit within the interior 100 of the ankle member 90 so that when the compressible member 110 is compressed, it deforms and presses against the interior sidewalls 92a,b of the ankle member, which, in turn, maintain its alignment with the forefoot member 30 and heel member 60. For this reason, it is preferred that the height H, width W, and thickness T of the compressible member 110 be such that it fits snugly within the ankle member 90 so that the ankle member's interior walls either touch it or nearly touch it when the compressible member 110 is not compressed. The preferred arrangement of the compressible member 110 with respect to the ankle member 90 is best shown in FIGS. 2 and 3. The shape of the compressible member 110 can be altered to correspond to the shape of the interior 100 of the ankle member 90. Accordingly, the compressible member 110 need not have the shape shown in every embodiment.

Limiting the lateral expansion of the compressible member 110 within the ankle member 90 is advantageous for many reasons, which include preventing destructive overstressing of the sheath 114 and changing the wearer's "feel" while walking to identify the need to replace the compressible member 110.

Although the compressible member 110 shown in the drawings and described here is particularly preferred, the compressible member 110 is not limited to this specific example. There are various other types of spring-like or shock absorbing devices that one having skill in the art, using this disclosure as guidance, may use to serve the same purpose.

Referring back now to FIG. 2, when the forefoot member 30 and heel member 60 are coupled to the ankle member 90 the lubricated posterior heel member surface 74 is in slidable contact with the ankle member posterior lubricated sidewall 104, the lubricated anterior forefoot member surface 46 is in slidable contact with the ankle member anterior lubricated sidewall 104, and the lubricated posterior forefoot member surface 48 is in slidable contact with the lubricated anterior heel member surface 76.

The lubricated surfaces are preferably formed from a solid lubricating material inlaid into the material that makes up the respective component part. The lubricating material allows the surfaces to slide quietly against each other with little wear. A particularly preferred lubricating material is polytetrafluoroethylene, commonly sold under the name TEFLON® by E.I. DuPont de Nemours and Company, Corp. Other suitable lubricating materials include, but are not limited to other families of fluoropolymers, polyethylene polymers of various molecular weights, acetal resins (commonly sold under the name DELRIN® by E.I. DuPont de Nemours and Company, Corp), or any other polymer that has good resistance to wear due to sliding.

Although not preferable, if desired, a liquid or gel-type lubricant can be applied to the lubricated surfaces for extra lubrication. One must be careful, however, in choosing the lubricant because grit trapped in the lubricant may damage the solid lubricating material.

As shown in FIGS. 1 and 2, pins 120 are positioned through the opposed lateral sidewalls 92b of the ankle member 90. Preferred pins 120 are shown in greater detail in FIGS. 20-23. Each pin 120 includes a cylindrical body 122 extending from a first end 123 to a wedge shaped second end 124. The pins 120 are preferably made from the same lubricating material as the lubricated surfaces, most preferably polytetrafluoroethylene, to allow the wedge shaped second end 124 to slide easily against the heel member 90 and forefoot member 30.

As best shown in FIGS. 2 and 24A-C, within the ankle member 90, the respective depressions 50, 78 of the forefoot member 30 and heel member 60 meet to form a pair of vertical guide slots that define the sliding direction in which the forefoot member 30 and heel member 60 slide. As best shown in FIG. 3, the pins 120 are positioned through the openings 102 in the ankle member 90 so that the wedge shaped second end 124 of each pin 102 fits within a respective guide slot. The pins 120 restrict the distance the forefoot member 30 and heel member 90 can slide to the length of the guide slots.

As mentioned above, the various components of the prosthetic foot 20 can easily be removed from the ankle member 90 without removing the ankle member 90 from the wearer's leg. This is advantageous for many reasons, some of which have already been described.

One of the particular advantages of the foot's modularity is that is allows one to easily replace the heel member 60 and forefoot member 30. An example of this is illustrated in FIGS. 24A-C in which a height of the heel end above ground G is adjusted by replacing heel member 60' with shorter heel member 60". This is achieved by sliding heel member 60' out of the ankle member 90 and sliding heel member 60" into the ankle member 90 as illustrated by the arrows in FIG. 24B. The guide pins (not shown) are installed as previously described. FIG. 24C shows the shorter heel member 60" installed on the prosthetic foot 20.

Figure 25:
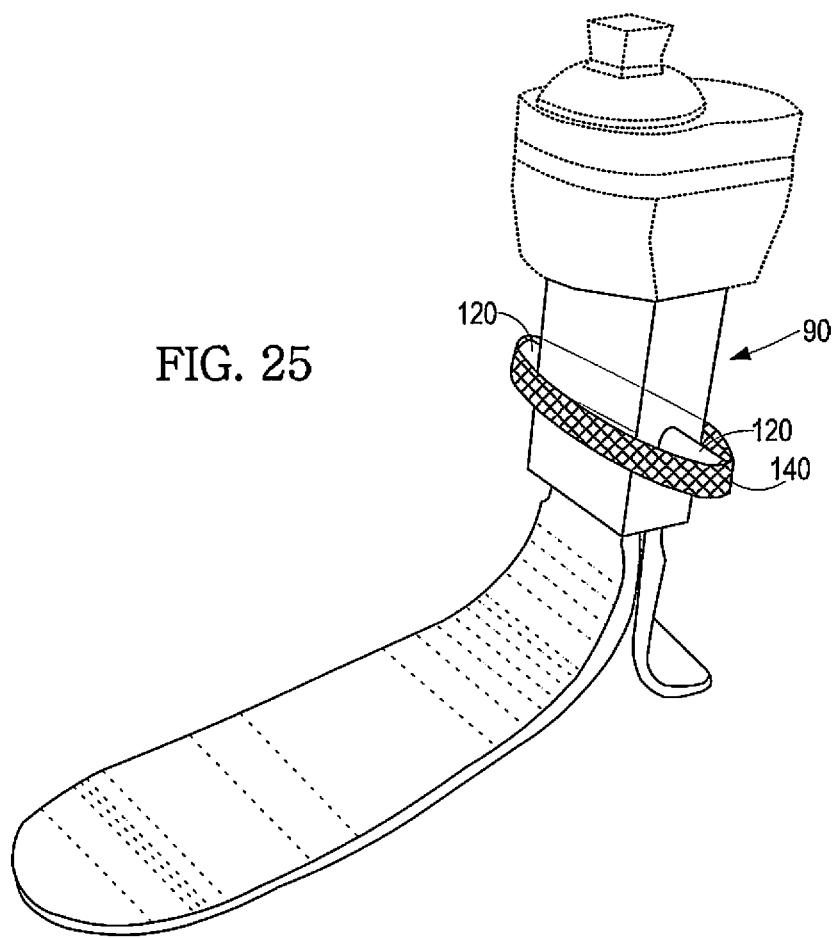
FIG. 25 is a side anterior perspective view of the prosthetic foot of FIG. 1 including a pin securing member.

Referring now to FIG. 25, it may be useful to include a pin securing member 140 to maintain the position of the pins 120. In the example shown, the pin securing member 140 is an annular strap that extends completely around the ankle member 90 and presses inwardly on the pins 120. There many different strap-type pin securing members 140 that are suitable, including resilient straps that can be stretched over the pins 120 or belt-like straps that include a fastener for joining two ends together. A preferred pin securing member 140 is a belt-like strap with a hook and loop type fastener. When used, the pin securing member 140 is preferably tightened around the pins 120 to prevent the pins from sliding out of the openings 102 while pressing the second end 124 of the pins 120 into the guide slots, which, in turn, causes the anterior lubricious surface 46 of the forefoot member and the posterior lubricious surface 74 of the heel member 90 to press against the lubricious surfaces 104 on the interior of the ankle member 90.

The prosthetic foot 20 may be made from any material suitable for making components parts of prosthetic devices and that can allow each of the components to perform its desired functions. The forefoot member 30, heel member 60, and ankle member 90 may be primarily made of the same or a different material. A particularly preferred material for making the forefoot member 30, heel member 60, and ankle member 90 is carbon fiber composite because it is lightweight, strong, and resilient. The properties of carbon fiber are also tunable to meet a desired need by varying the ply schedule, layer orientation, resins, and fabrication process employed to make each part.

The scope of the invention is not limited to the particular shape of the component shown in the drawings and described. The shape of each component may vary to account for a wearer's activity level and/or weight or may vary to be suited to a particular activity such as running.

The invention has been described in some detail, but it will be apparent that various modifications and changes can be made within the spirit and scope of the invention as described in the foregoing specification and the appended claims.

That which is claimed is:

1. A prosthetic foot comprising: a sleeve adapted to connect to the leg of a wearer with a limb connector positioned on the top of the sleeve; independent heel and forefoot members respectively simulating a heel and a forefoot portion of the wearer's foot, the heel and forefoot members being received within the sleeve in such a way that, when the wearer takes a step, the heel and forefoot members translate independently of one another along a vertical axis passing through the sleeve; and a compressible member in compressible contact with the heel and forefoot members in such a way that the compressible member compresses in response to the independent translation of the heel and forefoot members during the wearer's step.

2. The prosthetic foot of claim 1, wherein the compressible member is positioned within the sleeve, below the limb connector, and above the heel and forefoot members.

3. The prosthetic foot of claim 1, wherein the heel and forefoot members are in direct contact with the compressible member.

4. The prosthetic foot of claim 1, wherein the heel and forefoot members are made of carbon fiber.

5. The prosthetic foot of claim 1, wherein the heel and forefoot members include an inlay of solid lubricating material in the material forming the heel and forefoot members for lubricating surfaces on the heel and forefoot members that slide against the sleeve.

6. The prosthetic foot of claim 5, wherein the solid lubricating material includes polytetrafluoroethylene.

7. The prosthetic foot of claim 1, wherein the heel and forefoot members have a plate-like shape and are formed from a resilient material.

8. A prosthetic foot comprising: a heel member having a heel member shaft extending upwardly from a heel end thereof; a forefoot member having a forefoot member shaft extending upwardly from a toe end thereof; an ankle member defining a sleeve receiving the heel member shaft and forefoot member shaft within the sleeve in such a way that the heel member shaft and forefoot member shaft are translatable independently of one another along a vertical axis passing through the ankle member in response to a wearer taking a step; and a compressible member coupled to the ankle member, the compressible member being in contact with the heel member shaft and forefoot member shaft in such a way that the compressible member compresses in response to the independent translation of the forefoot member shaft and heel member shaft during the wearer's step; wherein the ankle member is adapted to connect to the leg of the wearer with a limb connector positioned on the top of the ankle member.

9. The prosthetic foot of claim 8, wherein the ankle member applies inward force to the heel member shaft and forefoot member shaft to maintain an alignment of the heel member shaft and forefoot member shaft therealong.

10. The prosthetic foot of claim 8, wherein the ankle member forms a sleeve around the heel member shaft and forefoot member shaft and the heel member shaft and forefoot member shaft translate upwardly within the sleeve when the heel member or forefoot member, respectively, contact the ground.

11. The prosthetic foot of claim 10, wherein the compressible member is positioned above the heel member shaft and forefoot member shaft within the sleeve.

12. The prosthetic foot of claim 11, wherein the ankle member applies inward force to the compressible member when the compressible member is compressed to maintain the compressible member's alignment with the heel member shaft and forefoot member shaft.

13. The prosthetic foot of claim 8, wherein the heel member shaft and forefoot member shaft are translatable along the vertical axis passing through the ankle member along or more guide slots passing through the ankle member, the one or more guide slots defining the direction of translation, each guide slot having a corresponding pin inserted therein to restrict translation of the heel member shaft and forefoot member shaft within a length of the one or more guide slots.

14. A prosthetic foot comprising: an ankle member having a sleeve defining an interior extending along a vertical axis passing through the ankle member, the ankle member having a compressible member positioned therein; a heel member having a heel member shaft extending upwardly from a heel end thereof and along the axis within the interior; and a forefoot member having a forefoot member shaft extending upwardly from a toe end and along the axis within the interior; wherein the heel member shaft and forefoot member shaft are translatable independently of one another along the axis in response to a wearer taking a step thereon and the compressible member compresses in response to the wearer's step; wherein the ankle member is adapted to connect to the leg of the wearer with a limb connector positioned on the top of the ankle member.

15. The prosthetic foot of claim 14, wherein the ankle member applies inward force to the heel member shaft and forefoot member shaft to maintain alignment of the heel member shaft and forefoot member shaft therealong.

16. The prosthetic foot of claim 14, wherein the compressible member is positioned above the heel member shaft and forefoot member shaft and intersects the axis.

17. The prosthetic foot of claim 16, wherein the ankle member applies inward force to the compressible member when the compressible member is compressed to maintain the compressible member's alignment with the heel member shaft and forefoot member shaft.

18. The prosthetic foot of claim 15, wherein the extent of translatability is defined by one more guide slots within the sleeve, extending along the axis, and having a corresponding pin inserted therein.

* * * * *